United States Patent [19]

Alper et al.

[11] Patent Number: 4,661,619

[45] Date of Patent: Apr. 28, 1987

[54] PROCESS FOR THE PRODUCTION OF CARBOXYLIC ACIDS AND/OR ESTERS THEREOF

[75] Inventors: Howard Alper, Ottawa, Canada; Sang C. Shim, Daegu, D.P.R. of Korea; David J. H. Smith, Camberley, England

[73] Assignee: The British Petroleum Company p.l.c., London, England

[21] Appl. No.: 676,077

[22] Filed: Nov. 29, 1984

[30] Foreign Application Priority Data

Nov. 30, 1983 [GB] United Kingdom ................. 8331981
Nov. 15, 1984 [GB] United Kingdom ................. 8428869

[51] Int. Cl.$^4$ ...................... C07C 69/76; C07C 51/12
[52] U.S. Cl. ..................................... 560/100; 560/55; 560/64; 560/103; 560/112; 560/232; 560/105; 562/517; 562/519
[58] Field of Search ................... 560/55, 64, 100, 103, 560/112, 105, 232; 562/406, 471, 517, 519; 170/165

[56] References Cited

U.S. PATENT DOCUMENTS 3,116,306 12/1963 Heck ................................. 560/232
3,784,573 1/1974 Fields et al. ........................ 560/103
3,845,121 10/1974 Eubanks et al. .................... 562/406
3,988,358 10/1976 Heck ................................... 560/64
4,323,694 4/1982 Scala, Jr. ............................ 560/103

OTHER PUBLICATIONS

*The Chemistry of Organic Compounds, Fourth ed.,* by J. B. Conant and A. H. Blatt; 1954 MacMillan Co., N.Y.; pp. 335–338.

*Carbon Monoxide in Organic Synthesis,* by J. Falbe; 1970 Springer-Verlag, N.Y.; pp. 116, 186–193.

Primary Examiner—Paul J. Killos
Attorney, Agent, or Firm—Brooks Haidt Hafner & Delahunty

[57] ABSTRACT

Carboxylic acids and/or esters thereof are produced by reacting either a benzylic or an aromatic mercaptan with carbon monoxide and either water or an aqueous alcohol at elevated temperature, suitably in the range from 100° to 300° C., in the presence as catalyst of a cobalt carbonyl, the product using water as the reactant being a carboxylic acid and using aqueous alcohol as the reactant a carboxylic acid ester, mixtures of acids and esters being formed using aqueous alcohols having high water concentrations.

10 Claims, No Drawings

PROCESS FOR THE PRODUCTION OF CARBOXYLIC ACIDS AND/OR ESTERS THEREOF

The present invention relates to a process for the production of carboxylic acids and/or esters thereof from benzylic and aromatic mercaptans.

Because of the long-term potential availability of carbon monoxide, a vast amount of research has been directed in recent times towards its utilisation in chemicals syntheses. This concentration of effort has led to commercial processes for the production of acetic acid by the reaction of methanol and carbon monoxide, and to another process whereby acetic anhydride is produced by the reaction of methyl acetate and carbon monoxide. Many other materials, for example alkyl halides, are reported to react with carbon monoxide but the development of commercial processes based on these reactions is still in the formative stages.

We have now found that benzylic and aromatic mercaptans will react with carbon monoxide and water to produce carboxylic acids and with aqueous alcohols to give carboxylic acid esters in the presence of suitable catalysts.

Accordingly, the present invention provides a process for the production of a carboxylic acid ester of the formula $RCOOR^1$ and/or a carboxylic acid of the formula $RCOOH$ which process comprises reacting at elevated temperature a mercaptan of the formula $RSH$ wherein R is a benzylic or an aromatic moiety with carbon monoxide and at least one compound of the formula $R^1OH$ wherein $R^1$ is either hydrogen or hydrogen and a hydrocarbyl group in the presence as catalyst of a cobalt carbonyl, the product comprising a carboxylic acid when $R^1OH$ is water and a carboxylic acid ester when $R^1OH$ is an aqueous alcohol.

In the formula RSH, R may be either a benzylic or an aromatic moiety. The benzylic moiety may be substituted in the benzene nucleus portion thereof by, for example hydrocarbyl groups such as alkyl groups, or by functional groups, such as for example halide or alkoxy groups. The aromatic moiety may be phenyl or naphthyl and may be substituted by for example a hydroxyl group or hydroxyl groups. Examples of suitable mercaptans of formula RSH which may be used in the process of the invention includes p-methylbenzyl thiol, o-methylbenzyl thiol, p-methoxybenzyl thiol, p-chlorobenzyl thiol, 2,4-dichlorobenzyl thiol, thiophenol, m-thiocresol and 2-naphthalene thiol.

Carbon monoxide may be obtained from a wide variety of carbonaceous sources using well-established conversion technology. The carbon monoxide may be pure or may contain such impurities as carbon dioxide, nitrogen or hydrogen. The carbon monoxide pressure may suitably be the autogenous pressure at the reaction temperature employed. Alternatively, carbon monoxide pressures in excess of the autogenous pressure, for example from 2 to 250 psig above the autogenous pressure, may suitably be employed.

As regards the compound(s) of formula $R^1OH$, there may be employed either water or an aqueous alcohol. Using water alone the product is a carboxylic acid. Using aqueous alcohols the product comprises carboxylic acid esters, generally free from carboxylic acids when the amount of water present is in the range from 5 to 12% by volume of the mixture. The presence of water is essential for the production of carboxylic acid esters. If water is omitted, hydrocarbons are formed in preference to esters, which reaction is the subject of our copending UK application No. 8413371, which corresponds to U.S. patent application Ser. No. 06/823,486 filed Jan. 6, 1986, (BP Case No. 5851). Clearly, it is possible to produce mixtures of carboxylic acids and carboxylic acid esters, for example when the proportion of water in the aqueous alcohol exceeds 12% by volume of the mixture.

The alcohol of formula $R^1OH$ may be a monohydric, dihydric or polyhydric alcohol. Thus $R^1$ may suitably be alkyl or hydroxyalkyl and may be straight-chain or branched-chain. Alternatively, $R^1$ may suitably be a cycloaliphatic or a cycloaromatic group. Examples of alcohols which may be used in the process of the invention include methanol, ethanol, propanols, butanols, pentanols, hexanols, for example 2-ethyl hexanol, and 1,4-butane diol. The amount of alcohol employed may suitably be at least the stoichiometric amount required to react with the mercaptan. It is preferred however, to employ a substantial excess of alcohol over the stoichiometric amount, the alcohol then performing the dual role of reactant and diluent for the reaction.

The catalyst is a cobalt carbonyl. This may be added as such or may be formed under the reaction conditions either during the reaction or in a separate preparative step in the absence of reactants. Thus, there may be added cobalt metal, suitably in finely divided form, or a cobalt compound, for example a soluble salt such as the nitrate, chloride or acetate. The cobalt carbonyl may suitably be added in an amount from 0.1 to 50% by weight of cobalt, based on the total weight of mercaptan employed.

A supplemental diluent may be employed if so desired. Suitable diluents include oxygenated hydrocarbons such as tetrahydrofuran.

The elevated temperature may suitably be in the range from 100° to 300° C., preferably from 150° to 250° C.

The process of the invention may be operated batchwise or continuously, preferably continuously.

The invention will now be further illustrated by reference to the following Examples.

EXAMPLE 1

To ethanol (30 ml) was added water (2 ml), p-methylbenzyl thiol (10 mmol) and dicobalt octacarbonyl (0.5 mmol). The mixture was heated to 185°-190° C. at 850-900 psi carbon monoxide pressure for 24 hours, after which the reaction mixture was filtered and the filtrate concentrated. The product was purified by silica gel chromatography and distillation.

EXAMPLE 2

The procedure of Example 1 was repeated except that methanol was used in place of ethanol.

EXAMPLE 3

The procedure of Example 1 was repeated except that isopropanol was used in place of ethanol.

EXAMPLE 4

The procedure of Example 1 was repeated except that t-butanol was used in place of ethanol.

EXAMPLE 5

The procedure of Example 1 was repeated except that o-methylbenzyl thiol was used in place of p-methylbenzyl thiol.

EXAMPLE 6

The procedure of Example 1 was repeated except that p-methoxybenzyl thiol was used in place of p-methylbenzyl thiol.

EXAMPLE 7

The procedure of Example 1 was repeated except that p-chlorobenzyl thiol was used in place of p-methylbenzyl thiol.

EXAMPLE 8

The procedure of Example 1 was repeated except that 2,4-dichlorobenzyl thiol was used in place of p-methylbenzyl thiol.

EXAMPLE 9

The procedure of Example 1 was repeated except that thiophenol was used in place of p-methylbenzyl thiol.

EXAMPLE 10

The procedure of Example 1 was repeated except that m-thiocresol was used in place of p-methylbenzyl thiol.

EXAMPLE 11

The procedure of Example 1 was repeated except that 2-napthalene thiol was used in place of p-methylbenzyl thiol.

The results of Examples 1 to 11 are given in Table 1.

TABLE 1
THE PRODUCTION OF CARBOXYLIC ACID ESTERS

| Example | Mercaptan | Alcohol* | Product | Yield (%) |
|---|---|---|---|---|
| 1 | P—$CH_3C_6H_4CH_2SH$ | A | p-$CH_3C_6H_4CH_2COOC_2H_5$ | 75 |
| 2 | " | B | p-$CH_3C_6H_4CH_2COOCH_3$ | 83 |
| 3 | " | C | p-$CH_3C_6H_4CH_2COOi$-$C_3H_7$ | 34 |
| 4 | " | D | p-$CH_3C_6H_4CH_2COOt$-$C_4H_9$ | 28 |
| 5 | o-$CH_3C_6H_4CH_2SH$ | A | o-$CH_3C_6H_4CH_2COOC_2H_5$ | 51 |
| 6 | p-$CH_3OC_6H_4CH_2SH$ | A | p-$CH_3OC_6H_4CH_2COOC_2H_5$ | 68 |
| 7 | p-$ClC_6H_4CH_2SH$ | A | p-$ClC_6H_4CH_2COOC_2H_5$ | 67 |
| 8 | 2,4-$Cl_2C_6H_3CH_2SH$ | A | 2,4-$Cl_2C_6H_3CH_2COOC_2H_5$ | 25 |
| 9 | Thiophenol | A | Ethyl benzoate | 82 |
| 10 | m-Thiocresol | A | Ethyl m-toluate | 47 |
| 11 | 2-Naphthalenethiol | A | 2-$C_{16}H_7COOC_2H_5$ | 50 |

*A = $C_2H_5OH$
B = $CH_3OH$
C = i-$C_3H_7OH$
D = t-$C_4H_9OH$

EXAMPLE 12

To water (30 ml) was added p-methylbenzyl thiol (10 mmol) and dicobalt octacarbonyl (0.5 mmol). The mixture was heated to 185°–190° C. at 850–900 psi carbon monoxide pressure for 24 hours, after which the reaction mixture was filtered and the filtrate concentrated. The product was purified by silica gel chromatography and distillation.

EXAMPLE 13

The procedure of Example 12 was repeated except that p-methoxybenzyl thiol was used in place of p-methylbenzyl thiol.

EXAMPLE 14

The procedure of Example 12 was repeated except that p-chlorobenzyl thiol was used in place of p-methylbenzyl thiol.

EXAMPLE 15

The procedure of Example 12 was repeated except that o-methylbenzyl thiol was used in place of p-methylbenzyl thiol.

EXAMPLE 16

The procedure of Example 12 was repeated except that thiophenol was used in place of p-methylbenzyl thiol.

EXAMPLE 17

The procedure of Example 12 was repeated except that m-methylbenzyl thiol was used in place of p-methylbenzyl thiol.

EXAMPLE 18

The procedure of Example 12 was repeated except that 2-napthalenethiol was used in place of p-methylbenzyl thiol.

The results of Examples 12 to 18 are given in the following Table 2.

TABLE 2
THE PRODUCTION OF CARBOXYLIC ACIDS

| Example | Mercaptan RSH | Product | Yield (%) |
|---|---|---|---|
| 12 | R = p-$CH_3C_6H_4CH_2$ | RCOOH | 30 |
| 13 | R = p-$CH_3OC_6H_4CH_2$ | RCOOH | 28 |
| 14 | R = p-$ClC_6H_4CH_2$ | RCOOH | 72 |
| 15 | R = o-$CH_3C_6H_4CH_2$ | RCOOH | 16 |
| 16 | R = Ph | RCOOH | 42 |
| 17 | R = m-$C_6H_4CH_2$ | RCOOH | 81 |
| 18 | R = 2-naphthyl | RCOOH | 59 |

We claim:

1. A process for the production of a carboxylic acid ester of the formula $RCOOR^1$ and/or a carboxylic acid of the formula RCOOH which process comprises reacting at elevated temperature, in the range from 100° to 300° C., a mercaptan of the formula RSH wherein R is an aromatic moiety with carbon monoxide and at least one compound of the formula $R^1OH$ wherein $R^1$ is either hydrogen or hydrogen and a hydrocarbyl group in the presence as catalyst of a cobalt carbonyl, the product comprising a carboxylic acid when $R^1OH$ is water and a carboxylic acid ester when $R^1OH$ is aqueous alcohol.

2. A process according to claim 1 wherein a mercaptan of the formula RSH is reacted with carbon monoxide and an aqueous alcohol to produce a carboxylic acid ester.

3. A process according to claim 2 wherein the amount of water present is in the range from 5 to 12% by volume of the aqueous alcohol mixture.

4. A process according to claim 2 wherein the amount of alcohol employed is at least the stoichiometric amount required to react with the mercaptan.

5. A process according to claim 1 wherein a mercaptan of the formula RSH is reacted with carbon monoxide and water to produce a carboxylic acid ester.

6. A process according to claim 1 wherein the temperature is in the range from 150° to 250° C.

7. A process according to claim 1 wherein a supplemental diluent selected from oxygenated hydrocarbons is employed.

8. A process according to claim 1, wherein the cobalt carbonyl is added in an amount from 0.1 to 50% by weight of cobalt, based on the total weight of mercaptan employed.

9. A process according to claim 1, wherein the alcohol $R^1OH$ is selected from the group consisting of methanol, ethanol, isopropanol, t-butanol, 2-ethyl hexanol, and 1,4-butanediol.

10. A process according to claim 1, wherein said mercaptan of formula RSH is selected from the group consisting of p-methylbenzyl thiol, o-methylbenzyl thiol, p-methoxybenzyl thiol, p-chlorobenzyl thiol, 2,4-dichlorobenzyl thiol, thiophenol, m-thiocresol and 2-naphthalene thiol.

* * * * *